United States Patent [19]
Loh et al.

[11] Patent Number: 5,743,892
[45] Date of Patent: Apr. 28, 1998

[54] DUAL FOAM CONNECTION SYSTEM FOR PERITONEAL DIALYSIS AND DUAL FOAM DISINFECTANT SYSTEM

[75] Inventors: Eric P. Loh, Park Ridge, Ill.; Randy Murphey, Kenosha, Wis.; Robin Peters, McHenry, Ill.; Scott D. Edwards, Libertyville, Ill.; Rafael A. Castellanos, Roselle, Ill.; Ying-Cheng Lo, Green Oaks, Ill.

[73] Assignee: Baxter International Inc., Deerfield, Ill.

[21] Appl. No.: 622,969

[22] Filed: Mar. 27, 1996

[51] Int. Cl.⁶ ............................................. A61M 25/00
[52] U.S. Cl. ..................................... 604/283; 604/905
[58] Field of Search ................................... 604/283, 905

[56] References Cited

U.S. PATENT DOCUMENTS

| | | |
|---|---|---|
| 4,354,490 | 10/1982 | Rogers. |
| 4,440,207 | 4/1984 | Genatempo et al. |
| 4,551,146 | 11/1985 | Rogers. |
| 4,655,762 | 4/1987 | Rogers. |
| 4,810,241 | 3/1989 | Rogers. |
| 5,340,359 | 8/1994 | Badia .......................... 604/905 |

FOREIGN PATENT DOCUMENTS

| | | |
|---|---|---|
| 0 183 396 | 10/1985 | European Pat. Off. |
| 0 227 219 | 9/1986 | European Pat. Off. |
| 0256640 | 2/1988 | European Pat. Off. |
| 2506162 | 11/1982 | France ......................... 604/905 |
| 8300812 | 3/1983 | WIPO. |

*Primary Examiner*—Michael Buiz
*Assistant Examiner*—Julian W. Woo
*Attorney, Agent, or Firm*—Thomas S. Borecki; Charles R. Mattenson; Robert M. Barrett

[57] ABSTRACT

A connector assembly and disinfectant system is provided for any system requiring a connection, such as during a peritoneal dialysis procedure. The connector assembly includes a transfer set connector and a disposable connector. The transfer set connector and disposable connector each include a member that join to create a fluid path. The disposable connector contains a housing that includes a ring partially saturated with disinfectant for bathing the transfer set member near the opening of the fluid path when a connection is made. The ring forms an opening through which the transfer set member passes. At disconnection, the transfer set member passes through a section of the ring having wiping properties to wipe the member dry.

19 Claims, 3 Drawing Sheets

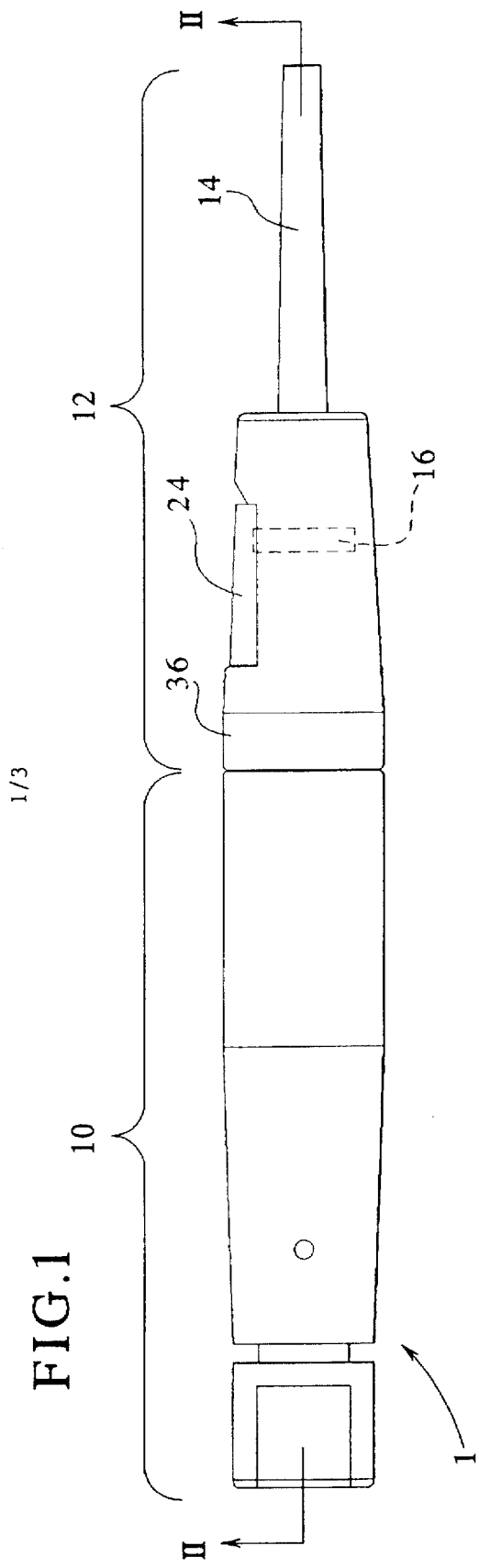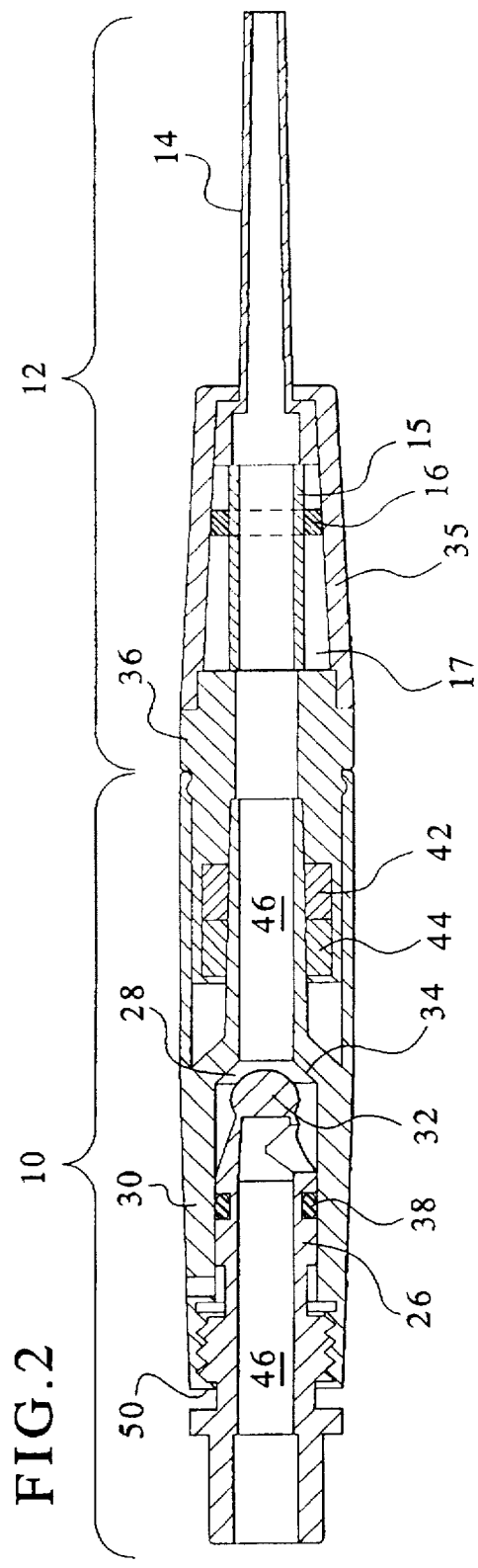

DUAL FOAM CONNECTION SYSTEM FOR PERITONEAL DIALYSIS AND DUAL FOAM DISINFECTANT SYSTEM

BACKGROUND OF THE INVENTION

The present invention generally relates to a connection system and method for peritoneal dialysis. More specifically, the invention relates to a connection system, used in peritoneal dialysis, having a disinfectant system that allows for disinfection at connection without additional effort or mess.

In peritoneal dialysis, a dialysate fluid is drawn from a source, e.g. a bag, and delivered via an external catheter to a peritoneal catheter that is implanted in the patient's peritoneal cavity. A connector connects the external catheter to the peritoneal catheter. The connector is required to withstand numerous connections and disconnections. Equally important to the successful treatment of renal patients using peritoneal dialysis is that an effective means exists for disinfecting this connection.

Typically, the method for disinfection involves immersion in povidone iodine, betadine or another messy disinfectant. Such a system requires more effort by the user prior to and after disinfection.

Additionally, the greater the number of manipulations of the disinfecting connection, the greater is the risk of peritonitis, a potentially dangerous complication of peritoneal dialysis.

Typically, staphylococci and other pathogens travel down the lumen of the catheter and enter the peritoneal cavity once a disinfecting technique has been neglected.

Peritonitis can be painful and temporarily diminishes the hydraulic permeability of the peritoneal membrane, rendering the renal treatment less successful. More resistant infections, leading to septicemia and death, can occur. Of the patients who abandon peritoneal dialysis, most do so because of repeated infections.

Because many patients perform the entire continuous ambulatory peritoneal dialysis (CAPD) procedure themselves, manipulations of the disinfecting connection often result in a contaminated system when the method of disinfection is too complicated or inconvenient for the patient. If breaks in the disinfecting connection system cannot be performed without contaminating the system, the entire system or at least the contaminated components must be replaced, thus increasing potential complications and costs of the treatment.

Today in the health care setting, simple and effective procedures that promote patient independence are becoming an important goal for outpatients, including (CAPD) patients.

Therefore, a need exists for an improved system of disinfection for connection systems in peritoneal dialysis applications as well as a method for providing peritoneal dialysis.

SUMMARY OF THE INVENTION

The present invention provides an improved system and method for ensuring disinfection when establishing fluid communication between a first site and a second site.

To this end, in an embodiment of the present invention, a connector system is provided for enabling fluid flow. The system has a fluid pathway defined by a first fluid pathway and a second fluid pathway. A ring having an opening is further provided. The ring is disposed within the second fluid pathway and includes a first section having absorbent properties and a second section having wiping properties. Further, the first section contains a disinfectant.

In an embodiment, the second housing is constructed and arranged so as to prevent the first section and the second section from moving within the connector system.

In an embodiment, the first section is adjacent to the second section.

In an embodiment, one of the sections is dry.

In an embodiment, the first section and the second section are integrally formed.

In an embodiment, an integrated clamp is located within the first housing.

In an embodiment, the first member and the second member are substantially in constant contact with the disinfectant until disconnection.

In an embodiment, a frangible is operatively connected to the second housing wherein the frangible is detachable from the second housing.

In another embodiment of the present invention, a system is provided for disinfecting a connection. The system has a first fluid pathway, a second fluid pathway, and a connector that connects the first fluid pathway and the second fluid pathway. The connector establishes fluid communication therebetween. A housing is within the connector wherein the housing includes a ring, the ring including a first section without disinfectant and a second section with disinfectant. A means for receiving a member to be disinfected through the ring is further provided.

In an embodiment, the second section is foam.

In an embodiment, the first section and the second section are integrally formed.

In an embodiment, the housing is constructed and arranged to prevent the ring from moving.

In another embodiment of the present invention, a method is provided for providing peritoneal dialysis. The method comprises the steps of: providing a first member in fluid communication with a supply of dialysate; providing a second member in fluid communication with a peritoneal cavity of a patient; providing a connector which, when attached, provides selective fluid communication between the first member and the second member; providing a ring within the connector, the ring including a first section with wiping properties and a second section with absorption properties; passing the first member through the ring at connection; and retracting the first member back through the ring at disconnection.

In an embodiment, the first member passes through the first section prior to the second section at connection.

In an embodiment, the first member is in substantially constant contact with the second section during connection.

In an embodiment, the first section is placed adjacent to the second section.

In an embodiment, the ring is constructed and arranged to include an opening in fluid communication with the first member.

In an embodiment, means is provided for sealing a connection between the first member and the second member.

Yet another embodiment of the present invention provides a housing defining an interior. A first piece having absorption properties is located within the interior. A second piece having wiping properties is located within the interior. The second piece is adjacent to the first piece. A disinfectant is contained within the first piece. An opening is provided through the first piece and the second piece.

It is, therefore, an advantage of the present invention to provide an improved connection system.

Another advantage of the present invention is to provide an improved disinfectant system that can be used in connection systems to disinfect connector components.

Still further, an advantage of the present invention is to provide an easy and non-messy mode of disinfecting, requiring little or no additional effort by the user.

An additional advantage provided by the present invention is to provide a connection system that can be used in any system requiring a connection.

Moreover, another advantage of the present invention is to provide a connection system that does not require additional components.

Yet a further advantage of the present invention is to provide a connection system having simple sealing and locking methods.

Another advantage of the present invention is to provide a connection system having flow regulation in a portion thereof.

Yet another advantage of the present invention is to provide a connection system that allows for containment of a disinfectant.

A still further advantage of the present invention is to provide a connection system having the capacity to keep two connecting pieces in nearly constant contact with an antimicrobial substance.

Another advantage of the present invention is to provide a connection system using a disinfectant without creating a messy environment therearound.

Furthermore, an advantage of the present invention is to provide an improved system for allowing fluid connections and disconnections in continuous ambulatory peritoneal dialysis.

Additional features and advantages of the present invention are described and will be apparent from the detailed description of the presently preferred embodiments and from the drawings.

BRIEF DESCRIPTION OF THE DRAWINGS

FIG. 1 illustrates a plan view of an embodiment of a connector of the present invention.

FIG. 2 illustrates a cross-sectional view taken generally along the line II—II of FIG. 1 of a transfer set and a connector in a connected position.

DETAILED DESCRIPTION OF THE PRESENTLY PREFERRED EMBODIMENTS

Figure 3:
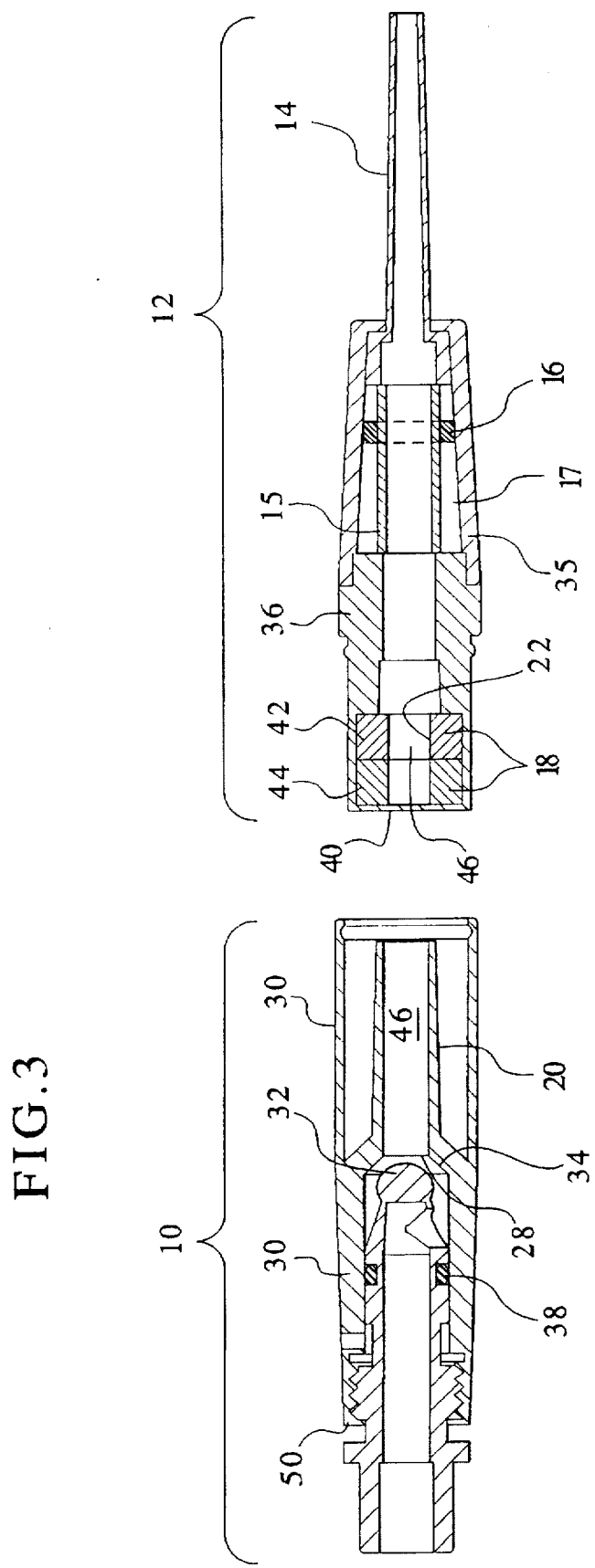
FIG. 3 illustrates a cross-sectional view of an embodiment of a transfer set and a connector in an unconnected position.

The present invention provides a connection system including a disinfecting system for any system requiring a connection, such as connection of a first length of tubing or other conduit to a second length of tubing or other conduit, such as for peritoneal dialysis. The present invention is designed to provide a safe and easy connection and disinfecting system for the user/patient without any mess. To this end, the present invention provides a disinfectant system used within a connection system.

Although, in a preferred embodiment, the method and system of the present invention can be used for peritoneal dialysis, it should be appreciated that the system and method can be used for a variety of other applications.

Pursuant to an embodiment of the present invention, the disinfectant system includes at least one ring. The ring may be a first piece without absorbent properties and a second piece with absorbent properties. The second piece, in a preferred embodiment, has a disinfectant incorporated therein. At connection, a member to be disinfected passes through the first piece; then the member passes through the second piece where the member is disinfected. At disconnection, when the member is retracted, the member passes back through the first piece where the member is wiped dry.

In a preferred embodiment, the second piece is a foam ring having open cell properties in which the disinfectant can be absorbed and held. The first piece is a material having closed cell properties, i.e. incapable of absorption, such that the first piece provides a wiping function. It should be understood, however, that the first piece and the second piece may be incorporated as a single piece having dual properties of absorption and non-absorption. Further, other materials other than foam may be implemented by those skilled in the art.

Referring now to the drawings, FIG. 1 generally illustrates an assembly 1 including a transfer set connector 10 and a disposable connector 12 in a connected position. In an embodiment, a clamp 16 (shown in FIG. 2) and a frangible 14 are integral parts of the disposable connector 12. The clamp 16 is integrated into the body of the disposable connector 12 to improve useability and, when activated, to prevent entrance of any contaminants from outside of the disposable connector 12.

In an embodiment, the clamp 16 is a C-type clamp having an arm that is depressible between a first position that compresses tubing 15 connected in an area 17 of the connector 12 in which the clamp 16 is housed when the connector 12 is connected to the transfer set connector 10. Of course, it should be understood that other clamping methods may be implemented by those skilled in the art. The important feature of the clamp 16 is that the clamp 16 is functionally integrated in the area 17 of the connector 12. As a result, when a button 24 of the connector 12 is depressed, the clamp 16 may be forced to a position that depresses the tubing 15 so as to prevent flow in the tubing 15.

As further illustrated in FIGS. 1 and 2, the connector 12, in an embodiment, is constructed from two portions. The connecting member 36 attaches to the transfer set connector 10 at one end and to the tubing 15 at its opposite end. Then, the connector housing 35 attaches to the connecting member 36 in a conventional manner so as to enclose the tubing 15 and the clamp 16 in the area 17 defined between the connecting member 36 and the connector housing 35.

The frangible 14 and the clamp 16 allow the user/patient to clamp the tubing 15 then break away the frangible 14. The frangible 14 is constructed and arranged such that breakage occurs slightly inside of the connector housing 35. This feature helps limit the irritation that could occur to the user/patient, such as a peritoneal dialysis patient. Additionally, the proximity of the clamp 16 and the frangible 14 reduces the amount of residual volume that can accumulate.

In the preferred embodiment illustrated, the button 24 is located on top of the disposable connector 12. The button 24, when depressed, occludes the tubing 15. The frangible 14 is then broken by holding the connected assembly 1 and snapping off the end of the frangible 14.

Referring to FIG. 2, the transfer set connector 10 and the disposable connector 12 are shown in the connected position. An opening 28 is situated at a point intermediate ends of the transfer set connector 10. The opening 28 of the transfer set connector 10 may be opened or closed in any manner known in the art, thereby increasing and decreasing the fluid flow through a fluid path 46.

An opening 28 is provided within a housing 30 of the transfer set connector 10 and an integrated clamp 26. The housing 30 is rigid and in a fixed position relative to the integrated clamp 26, which is both rigid and in an unfixed position. The integrated clamp 26 moves linearly from a point exterior to the outside of the housing 30 to the inside of the housing 30 through the end 50. The opening 28 widens as the integrated clamp 26 is retracted, increasing the flow rate of the fluid path 46. A ball 32 presses against a conical end 34 leading to the opening 28 to create a mechanical seal thus clamping off the fluid path 46. An 0-ring 38 located inside the housing 30 effectuates the seal. When the clamp 26 is retracted, the ball 32 retracts allowing fluid flow. Fluid flow can be increased by further retraction of the ball 32. Of course, other valving mechanisms, other than the ball 32, may be implemented by those skilled in the art. Alternatively, the transfer set connector 10 does not require a flow regulation mechanism.

Referring now to FIG. 3, the transfer set connector 10 and the disposable connector 12 are shown in an unconnected state. The transfer set connector 10 has a hollow, tapered member 20 within the housing 30. The disposable connector 12 has a similarly-sized hollow, tapered member 22. Telescopic insertion of the hollow, tapered member 20 into the hollow, tapered member 22 creates fluid communication between the fluid path 46 and the tubing 15 of the disposable connector 12. Sealing of the fluid path 46 occurs due to the differences in the hollow, tapered member 20 and the hollow, tapered member 22, one member being rigid and the other member being semi-rigid resulting in a mechanical seal.

The locking of the hollow, tapered member 20 to the hollow, tapered member 22 can be achieved independently of the sealing by use of an annular snap fit or any other method known in the art. The snap fit is designed to be activated after the seal has been established.

To further reduce the risk of "touch contamination", the transfer set connector 10 and the disposable connector 12 may be shrouded. If the transfer set connector 10 and the disposable connector 12 are shrouded, a groove (not shown) is located on the transfer set connector 10 and a bead (not shown) is provided on the disposable connector 12. If the transfer set connector 10 and the disposable connector 12 are not shrouded, then the groove is located on the disposable connector 12 and the bead is located on the transfer set connector 10.

In FIG. 3, a dual foam disinfectant system 18 is shown located in the disposable connector 12 at or near an end 40 of the disposable connector 12. At connection, the hollow tapered member 20 of the transfer set connector 10 passes through the disinfectant system 18. The hollow tapered member 20 can remain in nearly constant contact with the disinfectant during connection.

Figure 4:
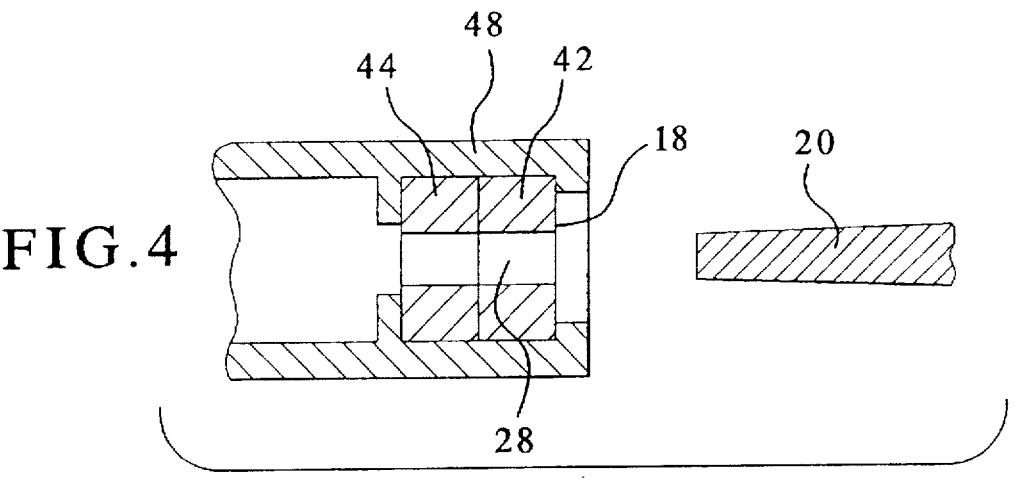
FIG. 4 illustrates a cross-sectional view of an embodiment of a housing including two adjacent pieces therein.

Referring now to FIG. 4, the disinfectant system 18 is shown having a housing 48, a non-absorbent piece 42 and a second absorbent piece 44.

In a preferred embodiment of the present invention, the first piece 42 has no disinfectant, and is, therefore, capable of wiping a liquid or gelatinous surface dry. The second piece 44 has absorbent properties capable of incorporating a disinfectant for disinfecting a member that contacts the second piece 44. The type of materials used to form the pieces 42,44 may vary and may be implemented by those skilled in the art. In a preferred embodiment, open cell materials are used, such as foam, for the second piece 44, and closed cell materials are used for the first piece 42. Those skilled in the art may, of course, implement other materials having absorption and wiping properties.

In an embodiment of the present invention, the first piece 42 is adjacent to the second piece 44 in the housing 48. The housing 48 is constructed to prevent the two pieces 42, 44 from moving after incorporation in the housing 48. As previously mentioned, the two pieces 42,44 may be formed as a single piece having at least two properties of absorption and wiping.

In another embodiment of the present invention, each of the pieces 42, 44 may include a disinfectant. The first piece 42 has less disinfectant than the second piece 44 and is not absorbent. The second piece 44 must be capable of wiping the member containing disinfectant dry.

At connection of the transfer set connector 10 and the disposable connector 12, the member 20 of the transfer set connector 10 is inserted into an opening 28 and passes through the first piece 42 and then the second piece 44 of the disposable connector 12, at which time the member 20 is coated with disinfectant. Upon disconnection of the transfer set connector 10 and the disposable connector 12, the first piece 42 wipes the member 20 of the transfer set connector 10 dry.

Figure 5:
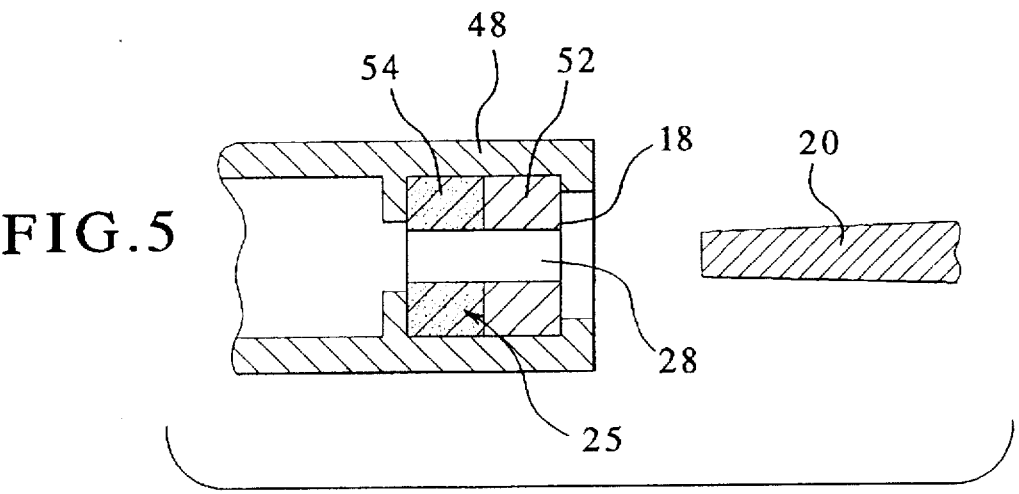
FIG. 5 illustrates a cross-sectional view of an embodiment of a housing including a single piece having an area with disinfectant and an area with little or no disinfectant.

In another embodiment, as illustrated in FIG. 5, a single piece 25 of material, may be implemented for the disinfectant system 18, instead of two separate pieces. Pursuant to the present invention, when a single piece is used, a first area 52 within the piece 25 contains little or no disinfectant and a second area 54 within the piece 25 contains substantially more disinfectant. The single piece 25 also includes an opening to receive a member for disinfection.

When the transfer set connector 10 is connected to the disposable connector 12 in the single piece system illustrated, the member 20 is inserted into an opening 28 and passes through the first area 52 and then the second area 54, at which time the member 20 is coated with disinfectant. At disconnection of the transfer set connector 10 and the disposable connector 12, the member 20 is retracted, and the first area 52 of the single piece 25 wipes the member 20 dry.

Figure 6:
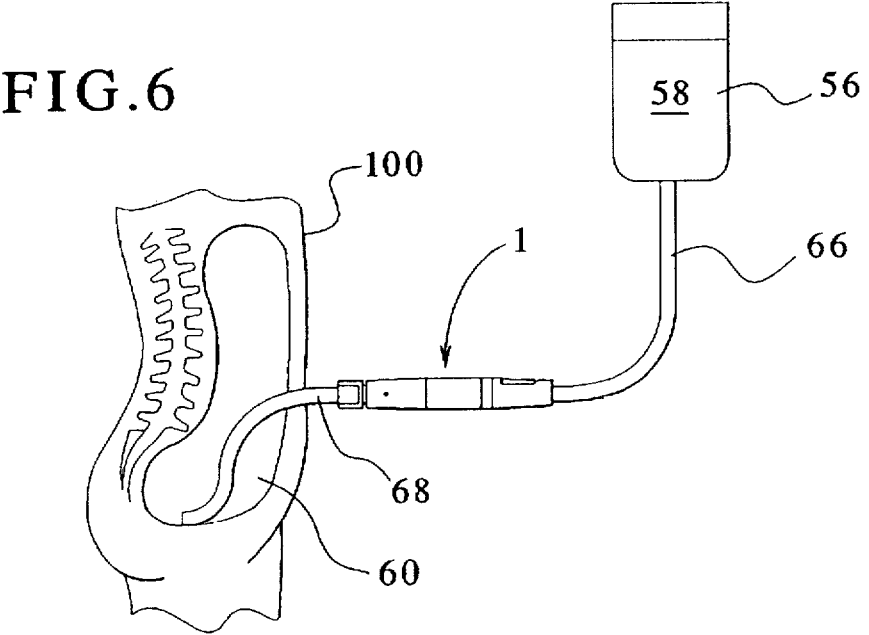
FIG. 6 illustrates an embodiment of a method of use of the connector of the present invention in a system for conducting peritoneal dialysis.

Pursuant to an embodiment of the present invention, a method for using the connector assembly 1 during a peritoneal dialysis procedure is illustrated in FIG. 6. A first tubing 66 is in fluid communication with an interior of a bag 56 including a supply of dialysate 58. A second tubing or transfer set tubing 68 is in fluid communication with a catheter which is implanted in a peritoneal cavity 60 of a patient 100. The connector assembly 1 of the present invention provides selective fluid communication between lengths of tubings 66,68 connecting the bag 56 to the peritoneal cavity 60 of the patient.

Upon connection of the transfer set tubing 68 to the transfer set connector 10 of the connector assembly 1 and subsequent connection of the disposable connector with the first tubing 66, disinfection takes place with the absorbent and non-absorbent pieces within the connector assembly 1.

It should be understood that various changes and modifications to the presently preferred embodiments described herein will be apparent to those skilled in the art. Such changes and modifications can be made without departing from the spirit and scope of the present invention and without diminishing its attendant advantages. It is, therefore, intended that such changes and modifications be covered by the appended claims.

We claim:

1. A connector system for enabling fluid flow, the system comprising:

a first housing having a first fluid pathway;

a second housing having a second fluid pathway; and a ring having an opening, disposed within the second fluid pathway, the ring including a first section having absorbent properties and a second section having wiping properties, the first section containing a disinfectant.

2. The connector system of claim 1 wherein the second housing is constructed and arranged so as to prevent the first section and the second section from moving within the connector system.

3. The connector system of claim 1 wherein the first section is adjacent to the second section.

4. The connector system of claim 1 wherein one of the sections is dry.

5. The connector system of claim 1 wherein the first section and the second section are integrally formed.

6. The connector system of claim 1 further comprising:

an integrated clamp located with the first housing.

7. The connector system of claim 5 wherein the first housing and the second housing are substantially in constant contact with the disinfectant until disconnection.

8. The connector system of claim 1 further comprising:

a frangible operatively connected to the second housing wherein the frangible is detachable from the second housing.

9. A system for disinfecting a connection, the system comprising:

a first fluid pathway member;

a second fluid pathway member;

a connector that connects the first fluid pathway member and the second fluid pathway, member the connector establishing fluid communication therebetween;

a housing within the connector, the housing including a ring, the ring including a first section without disinfectant and a second section with disinfectant; and means for receiving a fluid pathway member to be disinfected through the ring.

10. The system of claim 9 wherein the second section is foam.

11. The system of claim 9 wherein the first section and the second section are integrally formed.

12. The system of claim 9 wherein the housing is constructed and arranged to prevent the ring from moving.

13. A method for providing peritoneal dialysis, the method comprising the steps of:

providing a first member in fluid communication with a supply of dialysate;

providing a second member in fluid communication with a peritoneal cavity of a patient;

providing a connector which, when attached, provides selective fluid communication between the first member and the second member;

providing a ring within the connector, the ring including a first section with wiping properties and a second section with absorption properties;

passing the first member through the ring at connection; and retracting the first member back through the ring at disconnection.

14. The method of claim 13 wherein the first member passes through the first section prior to the second section at connection.

15. The method of claim 13 further comprising the step of:

allowing the first member to be in substantially constant contact with the second section during connection.

16. The method of claim 13 further comprising the step of:

placing the first section adjacent to the second section.

17. The method of claim 13 wherein the ring is constructed and arranged to include an opening in fluid communication with the first member.

18. The method of claim 13 further comprising the step of:

providing a means for sealing a connection between the first member and the second member.

19. A connector comprising:

a housing defining an interior;

a first piece having absorption properties located within the interior;

a second piece having wiping properties located within the interior, the second piece adjacent to the first piece;

a disinfectant within the first piece; and an opening through the first piece and the second piece.

* * * * *